United States Patent
Jordan

(10) Patent No.: US 6,978,781 B1
(45) Date of Patent: Dec. 27, 2005

(54) NASAL DILATOR

(76) Inventor: John Jordan, 270 Mulberry St., Jacksonville, FL (US) 32208

( * ) Notice: Subject to any disclaimer, the term of this patent is extended or adjusted under 35 U.S.C. 154(b) by 0 days.

(21) Appl. No.: 11/078,870

(22) Filed: Mar. 11, 2005

(51) Int. Cl.[7] ............... A61M 16/00; A61M 15/08; A61F 5/08
(52) U.S. Cl. ............... 128/206.11; 128/207.18; 606/204.45
(58) Field of Search ............... 128/206.11, 207.18, 128/204.12, 200.24, 206.12, 206.18, 206.27, 128/207.13; 606/161, 162, 198, 199, 204.45

(56) References Cited

U.S. PATENT DOCUMENTS

| | | | |
|---|---|---|---|
| 1,256,188 A * | 2/1918 | Wilson | 606/199 |
| 2,010,485 A * | 8/1935 | Heath | 606/199 |
| 3,905,335 A * | 9/1975 | Kapp | 128/206.11 |
| 4,327,719 A * | 5/1982 | Childers | 128/206.11 |
| 5,665,104 A * | 9/1997 | Lee | 606/199 |
| 6,004,342 A * | 12/1999 | Filis | 606/199 |
| 6,270,512 B1 | 8/2001 | Rittmann | |
| 6,357,436 B1 | 3/2002 | Kreitzer | |
| 6,561,188 B1 | 5/2003 | Ellis | |
| 6,679,265 B2 | 1/2004 | Strickland | |
| 6,694,970 B2 | 2/2004 | Spinelli | |
| 6,769,429 B1 | 8/2004 | Benetti | |
| 6,776,162 B2 | 8/2004 | Wood | |
| 2004/0261791 A1 * | 12/2004 | Horian | 128/200.24 |

* cited by examiner

*Primary Examiner*—Teena Mitchell
(74) *Attorney, Agent, or Firm*—Lawrence J. Gibey, Jr.

(57) ABSTRACT

This is a device which will provide nasal dilation and yet will provide comfort for the user. It will be portable and easily installed or removed by the user.

3 Claims, 2 Drawing Sheets

NASAL DILATOR

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

A. Field of the Invention

This relates to dilating the nasal cavities so that an individual can breathe with less difficulty. It is portable and will conform to the general shape of a nose. It does not use any auxiliary equipment and is not designed to be connected to a cannula.

B. Prior Art

There are many devices related to nasal dilation including those patents related to nasal dilation and cannulas specifically. Additionally, there are nasal dilators, which dilate internally and those that dilate externally. Examples of the prior art include Ellis U.S. Pat. No. 6,561,188, Strickland, U.S. Pat. No. 6,679,265 and Rittman, U.S. Pat. No. 6,270,512. Ellis and Strickland contemplate dilation with a cannula while the Rittman device contemplates a temporary dilation measure without a cannula.

The current device allows permanent dilation and does not incorporate the use of a cannula. The present device can be worn at all times. None of the other prior art has a beveled edge on the inner surface of the device. The beveled edge is necessary to insure a tight, comfortable fit.

BRIEF SUMMARY OF THE INVENTION

This device is comprised of two identical nasal dilators connected by a single string or cord. The nasal dilators have a flange on the top and bottom edges. The dilators are cylindrical and hollow and are designed to be inserted into the nasal cavity.

Each of the dilators has a beveled edge on each inner side between the top and bottom flanges. This beveled edge will allow the device to conform to the general shape of the nose for additional comfort of the user. The beveled edge will insure a secure fit within the interior of the nose. Additionally, the beveled edge will allow or permit the device to remain in the nose during normal operation.

Plastic is probably a preferred material for construction due to its cost and durability. The entire device will be cast as a single unit with a mold. The flanges, which are on the top and bottom of the respective annular openings will be plastic and part of that same mold. The purpose of the flanges is to provide a surface area for the device to grip the inside surface of the nose without causing irritation or damage to the interior of the nose.

It is an object of this device to provide nasal dilation, which is comfortable. It is another object to make the device portable and re-usable.

DETAILED DESCRIPTION OF THE EMBODIMENT

Figure 1:
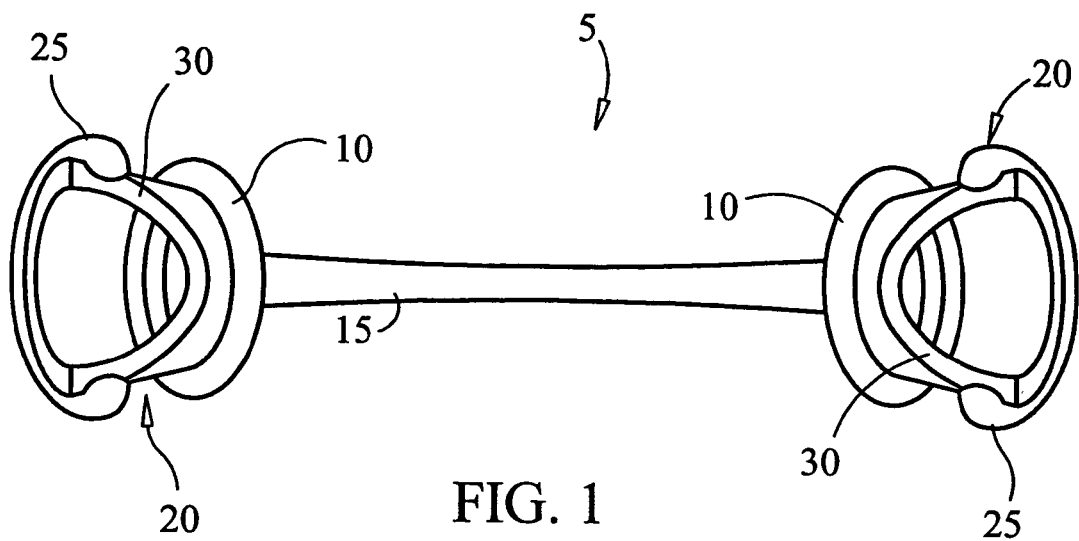
FIG. 1 is a front view of the device.
Figure 3:
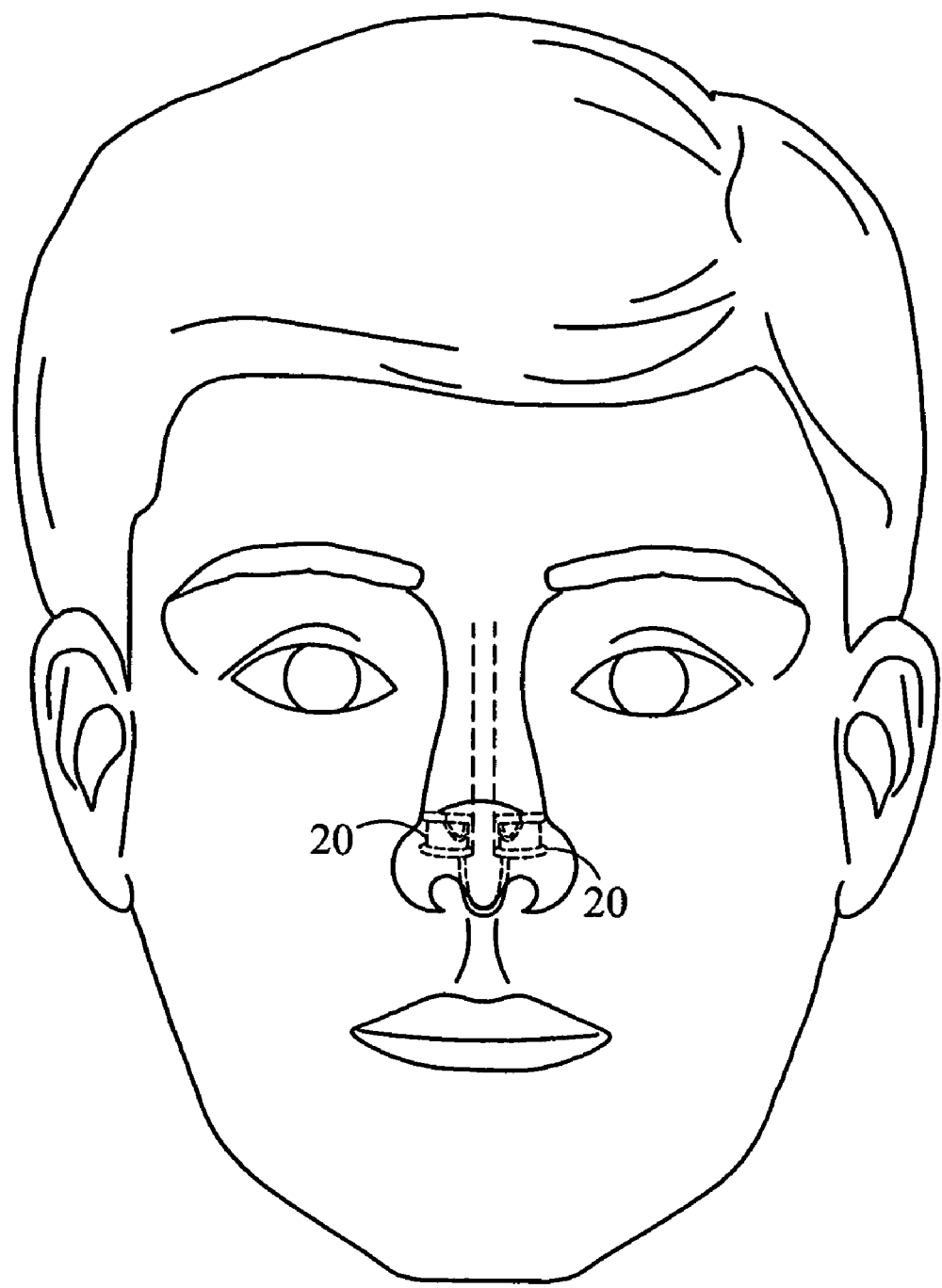
FIG. 3 is a view of the device inserted in the nasal cavity.

The device 5 is comprised of two separate nasal dilators 20 joined by a cord 15. FIG. 1, 2 The nasal dilators 20 are cylindrical and hollow and are designed to be inserted into a person's nasal cavities. FIG. 3.

A flange is provided on the top surface 25 and the bottom surface 10 of the nasal dilators. The flanges are installed to ensure a tight fit in the nose of the individual. The top flange 25 and bottom flange 10 are part of the molded device and are necessary to insure a secure fit within the nasal cavity.

Figure 2:
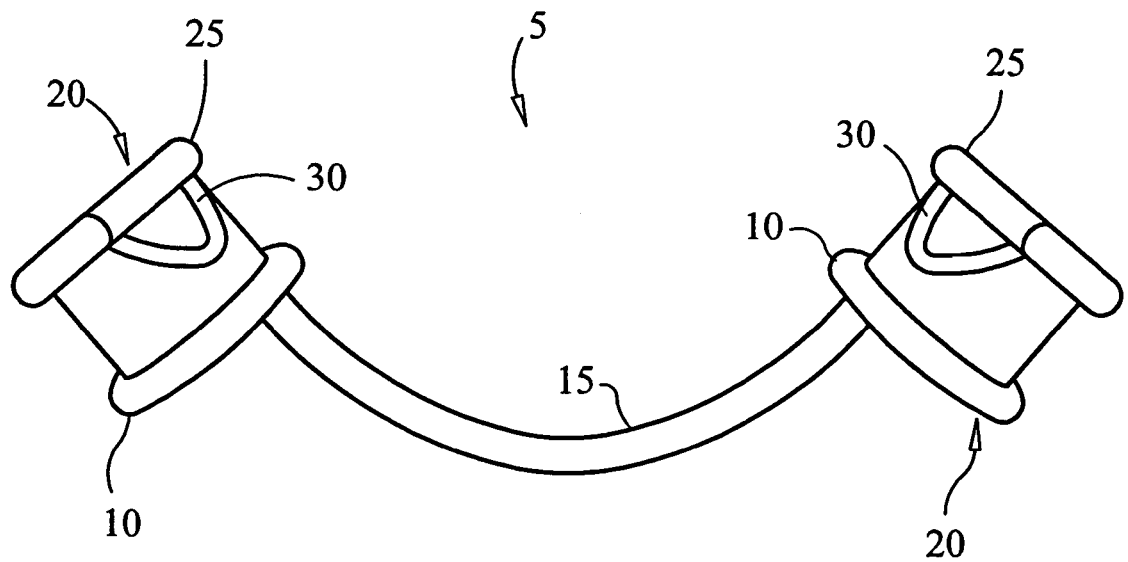
FIG. 2 is a side view of the device.

Additionally, a beveled edge 30 is placed on the interior surface of the respective nasal dilators 20 between the top flange 25 and the bottom flange 10 surfaces. FIGS. 1, 2 The beveled edge 30 will extend from the top flange 25 to the approximate midpoint on the cylindrical surface between the top flange 25 and the bottom flange 10. FIGS. 1, 2 The beveled edge 30 allows the device 5 to better conform to the shape of the nose of an individual and allows a more comfortable fit.

The two nasal dilators 20 are connected by a string 15 or cord so that the individual does not have separate nasal dilators 20 and that they remain together. The cord 15, which connects the two dilators 20, is manufactured as part of the mold.

The device 5 will be cast or molded as one piece. Plastic is probably the preferred choice of material due to its cost and durability and its relative comfort for the user.

It is anticipated that the flanges 10, 25 will be made as part of the mold and the device will likely be plastic. The use of plastic will allow comfort and yet some degree of elasticity to conform to a majority of nasal cavities. The device should also be washable and durable and plastic would accomplish that objective.

What is claimed is:

1. A nasal dilation device, which is comprised of:
   a. nasal dilators;
   b. flange on the bottom surface;
   c. flange on the top surface;
   d. a beveled edge;
   e. a cord;
   wherein a nasal dilator is used for each nasal cavity;
   wherein the nasal dilators are connected by a cord;
   wherein the nasal dilators are cylindrical and hollow;
   wherein the nasal dilators have a top surface and a bottom surface;
   wherein a flange on the bottom surface of the nasal dilator is provided;
   wherein a flange on the top surface of the nasal dilator is provided;
   wherein a beveled edge is placed between the top surface and the bottom surface of the nasal dilators.

2. The flange as described in claim 1 is constructed as an integral part of the nasal dilator.

3. The beveled edge as described in claim 1 wherein the beveled edge extends from the inside surface of the top flange to the approximate mid point of the device.

* * * * *

UNITED STATES PATENT AND TRADEMARK OFFICE
CERTIFICATE OF CORRECTION

PATENT NO.     : 6,978,781 B1
DATED          : December 27, 2005
INVENTOR(S)    : John Jordan It is certified that error appears in the above-identified patent and that said Letters Patent is hereby corrected as shown below:

<u>Title page,</u>
Item [74], *Attorney, Agent, or Firm*, should read -- Lawrence J. Gibney, Jr. --.

Signed and Sealed this

Sixteenth Day of May, 2006

JON W. DUDAS
*Director of the United States Patent and Trademark Office*